US006316613B1

(12) United States Patent
Chen et al.

(10) Patent No.: US 6,316,613 B1
(45) Date of Patent: Nov. 13, 2001

(54) CHIRAL SEPARATION OF PHARMACEUTICAL COMPOUNDS WITH CHARGED CYCLODEXTRINS USING CAPILLARY ELECTROPHORESIS

(75) Inventors: Fu-Tai A. Chen, Brea; Ramon A. Evangelista, Placentia; Gene G. Y. Shen, Diamond Bar; Chan S. Oh, Chino Hills, all of CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 08/910,483

(22) Filed: Jul. 25, 1997

(51) Int. Cl.$^7$ ............... C07H 1/00; C08B 37/16
(52) U.S. Cl. .......... 536/103; 536/46; 428/423.1; 428/426; 428/447; 428/532
(58) Field of Search ............... 536/46, 103; 428/423.1, 428/426, 447, 532

(56) References Cited

U.S. PATENT DOCUMENTS

| | | | |
|---|---|---|---|
| 5,183,809 | * | 2/1993 | Weisz et al. ............ 514/58 |
| 5,658,894 | * | 8/1997 | Weisz ..................... 514/58 |

OTHER PUBLICATIONS

Fanali, J. Chromatography, "Identification of chiral drugs . . . ", vol. 735, pp. 77–121, 1996.*
Nishi et al., J. Chromatography, "Optical resolution of drugs . . . ", vol. 694, pp. 245–276, 1995.*
Aldrich Chemical Company, Inc., Product Catalog, Milwaukee, WI, p. 414 (91996).
Chankvetadze, B., et al., About some aspects of the use of charged cyclodextrins for capillary electrophoresis enantioseparation, *Electrophoresis*, 15: 804 (1994).
Dette, C., et al., "Neutral and anionic cyclodextrins in capillary zone electrophoresis: Enantiometric separation of ephedrine and related compounds", *Electrophoresis*, 15: 799 (1994).
Fanali, S., "Identification of chiral drug isomers by capillary electrophoresis", *J. Chromatogr. A*, 735:77 (1996).
Guttman, A., "Capillary Electrophoresis Separation of Enantiomers by Cyclodextrin Array Chiral Analysis", *Handbook of Capillary Electrophoresis*, 2$^{nd}$ Ed. J..Landers, Ed. CRC Press, Boca Raton, Fl, Chapter 3, p. 75 (1997).

Lurie, I.S., et al., "Chiral Resolution of Cationic Drugs of Forensic Interest by Capillary Electrophoresis with Mixtures of Neutral and Anionic Cyclodextrins", *Anal. Chem.*, 66(22):4019 (1994).
Mayer, S., et al., "Dual Chiral Recognition System Involving Cyclodextrin Derivatives in Capillary Electrophoresis", *J. Microcol.*, 6:43 (1994).
Moriya, T., et al., "A New Candidate for an Anti–HIV–1 Agent: Modified Cyclodextrin Sulfate (mCDS71)", *J. Med. Chem.*, 36:1674 (1993).
Nishi, H., et al., "Optical Resolution of drugs by capillary electrophoretic techniques", *J. Chromatogr. A*, 694:245 (1995).
Stalcup, A.M., et al., "Application of Sulfated Cyclodextrins to Chiral Separations by Capillary Zone Electrophoresis", *Anal. Chem.*, 68:1360 (1996).
Tait, R.J., et al., "Sulfobutyl Ether βCyclodextrin as a Chiral Deiscriminator for Use with Capillary Electrophoresis", *Anal. Chem.*, 66:4013 (1994).
Terabe, S., et al., "Separation of enantiomers by capillary electrophoretic techniques", *J. Chromatogr. A*, 666:295 (1994).
Wu, W., et al., "Capillary Electrophoretic Chiral Separations Using a Sulfated β–Cyclodextrin–Containing Electrolyte", *J. Liq. Chromatogr.*, 18(7):1289 (1995).

* cited by examiner

*Primary Examiner*—Gary Geist
*Assistant Examiner*—Howard V. Owens, Jr.
(74) *Attorney, Agent, or Firm*—William H. May; Arnold Grant (57) ABSTRACT

The separation of enantiomeric pairs of compounds by capillary electrophoresis using highly sulfated α-, β-, and γ-cyclodextrins as chiral selectors is described herein. These charged cyclodextrins have a higher degree of sulfation and narrower heterogeneity than previous cyclodextrin derivatives. CE analyses using highly sulfated cyclodextrins produce improved resolution of a wide variety of chiral drugs, particulaly neutral compounds and amines. The highly sulfated α-,β-, and γ-cyclodextrins produce separations which complement each other to further expand the number of neutral and basic drugs that can be resolved by capillary electrophorsis.

25 Claims, 9 Drawing Sheets

CE ANALYSIS OF SULFATED CYCLODEXTRINS WITH INDIRECT UV DETECTION
40mM TOLUENESULFONATE pH 8.0, 10kV/13 μamp, 50 μm x 27 cm PVA, 254 nm

Fig. 1A

CE ANALYSIS OF SULFATED CYCLODEXTRINS WITH INDIRECT UV DETECTION
40mM TOLUENESULFONATE pH 8.0, 10kV/13 μamp, 50 μm x 27 cm PVA, 254 nm

Fig. 1B

CE ANALYSIS OF SULFATED CYCLODEXTRINS WITH INDIRECT UV DETECTION
40mM TOLUENESULFONATE pH 8.0, 10kV/13 µamp, 50 µm x 27 cm PVA, 254 nm

*Fig. 1C*

CE ANALYSIS OF SULFATED CYCLODEXTRINS WITH INDIRECT UV DETECTION
40mM TOLUENESULFONATE pH 8.0, 10kV/13 µamp, 50 µm x 27 cm PVA, 254 nm

*Fig. 2A*

CE ANALYSIS OF SULFATED CYCLODEXTRINS WITH INDIRECT UV DETECTION
40mM TOLUENESULFONATE pH 8.0, 10kV/13 μamp, 50 μm x 27 cm PVA, 254 nm

*Fig. 2B*

CE ANALYSIS OF SULFATED CYCLODEXTRINS WITH INDIRECT UV DETECTION
40mM TOLUENESULFONATE pH 8.0, 10kV/13 μamp, 50 μm x 27 cm PVA, 254 nm

*Fig. 2C*

CE ANALYSIS OF SULFATED CYCLODEXTRINS WITH INDIRECT UV DETECTION
40mM TOLUENESULFONATE pH 8.0, 10kV/13 μamp, 50 μm x 27 cm PVA, 254 nm

Fig. 3A

CE ANALYSIS OF SULFATED CYCLODEXTRINS WITH INDIRECT UV DETECTION
40mM TOLUENESULFONATE pH 8.0, 10kV/13 μamp, 50 μm x 27 cm PVA, 254 nm

CE ANALYSIS OF SULFATED CYCLODEXTRINS WITH INDIRECT UV DETECTION
40mM TOLUENESULFONATE pH 8.0, 10kV/13 μamp, 50 μm x 27 cm PVA, 254 nm

Fig. 4B

CE ANALYSIS OF SULFATED CYCLODEXTRINS WITH INDIRECT UV DETECTION
40mM TOLUENESULFONATE pH 8.0, 10kV/13 μamp, 50 μm x 27 cm PVA, 254 nm

Fig. 4C

CE SEPARATION OF AMPHETAMINE ENANTIOMERS SULFATED α, β AND γ CYCLODEXTRINS

5% SULFATED CYCLODEXTRIN, 25mM TEA PHOSPHATE pH 2.5, 3 s INJECTION, 214nm

*Fig. 5A*

CE SEPARATION OF AMPHETAMINE ENANTIOMERS SULFATED α, β AND γ CYCLODEXTRINS

5% SULFATED CYCLODEXTRIN, 25mM TEA PHOSPHATE pH 2.5, 3 s INJECTION, 214nm

*Fig. 5B*

CE SEPARATION OF AMPHETAMINE ENANTIOMERS
SULFATED α, β AND γ CYCLODEXTRINS

5% SULFATED CYCLODEXTRIN, 25mM TEA PHOSPHATE pH 2.5, 3 s INJECTION, 214nm

*Fig. 5C*

CE SEPARATION OF THALIDOMIDE ENANTIOMERS
SULFATED α, β AND γ CYCLODEXTRINS

5% SULFATED CYCLODEXTRIN, 25mM TEA PHOSPHATE pH 2.5, 3 s INJECTION, 214nm

CHIRAL SEPARATION OF PHARMACEUTICAL COMPOUNDS WITH CHARGED CYCLODEXTRINS USING CAPILLARY ELECTROPHORESIS

TECHNICAL FIELD OF THE INVENTION

The present invention relates generally to the use of cyclodextrins to separate optical isomers by capillary electrophoresis.

BACKGROUND OF THE INVENTION

Many chemical compounds used in pharmaceutical formulations possess an asymmetric center responsible for optical activity that can strongly influence their pharmacological properties. Examples of synthetic drugs in which one of two enantiomers possess a different pharmacological properties are well known. For example, (−)-propranolol is 100-fold more potent than (+)-propranolol. In addition one of two enantiomers of the same drug can be more toxic, e.g., thalidomide, ketamine. Accordingly, analytical methods that separate enantiomers with high resolution power and high efficiency are becoming increasingly important. The need for stereochemically pure drugs and careful testing of existing racemates necessitates the development of efficient, fast, sensitive and accurate chiral analysis methods.

Chromatography techniques, particularly high-performance liquid chromatography (HPLC), are commonly used for the analysis of enantiomers. More recently, capillary electrophoresis (CE) has been adapted for use in conjunction with chiral selectors. The most common strategy employed is the use of cyclodextrins for differential host-guest complexation of enantiomeric pairs [Fanali, S., J., *Chromatogr.*, 735:77–121 (1996); Nishi, H., and Terabe, S., J., *Chromatogr.*, 694:245–276 (1995); Guttman, A., "Capillary Electrophoresis Separation of Enantiomers by Cyclodextrin Array Chiral Analysis", pp. 75–100 in Handbook of Capillary Electrophoresis, 2nd Ed., J. Landers, Ed., 1997, CRC Press Inc., Boca Raton, Fla.]. In contrast to HPLC separations, in which one must select carefully from the wide variety of available columns containing the resolving agent bound to the solid support, chiral CE analyses are greatly simplified by having chiral selectors such as cyclodextrin dissolved in the separation buffer.

Cyclodextrins (CD) are cyclic oligosaccharides consisting of six, seven or eight glucose units corresponding to the names α-, β- or γ-cyclodextrin. CD's form a truncated cone with a rim of secondary hydroxy groups at the opening with the larger diameter. The internal cavity contains no hydroxy functions and exhibits a hydrophobic character. This hydrophobic nature permits CD's to form highly selective inclusion complexes with aromatic or alkyl groups. Differences in the complex formation constants of a CD and its guest molecules can effect the relative electrophoretic mobilities of structurally similar optical isomers, resulting in a clear separation of enantiomers.

In chiral separations of acidic and basic compounds, the CD complex migrates under the influence of the charge of the ionic analytes. For neutral analytes, however, uncharged cyclodextrins are not applicable because the analyte, the cyclodextrin and the complex have no electrophoretic mobilities. The use of charged cyclodextrins was therefore conceived to solve the problem for chiral separation of neutral compounds.

Mayer et al. [*J. Microcol. Sep.*, 6:43–48 (1994)] and Tait et al. [*Anal. Chem.*, 66:4013–41018 (1994)] first reported the use of a sulfobutyl ether, β-cyclodextrin (SBE-βCD) for CE chiral separations. Subsequent reports have described the analysis of amines and neutral compounds using SBECD as chiral selector [Dette et al., *Electrophoresis*, 15:799–803 (1994); Chankvetadze et al., *Electrophoresis*, 15:804–807 (1994); Lurie et al., *Anal. Chem.*, 66:4019–4026 (1994)]. Vincent et al. ("A family of novel, single-isomer chiral resolving agents for capillary electrophoresis. Part 2: Heptakis-6-sulfato-β-cyclodextrin, submitted to Analytical Biochemistry, Apr. 15, 1997) adapted the selective protection and deprotection methods of Moriya et al. [*J. Med. Chem.*, 36:1674–1677 (1993)] to synthesize a sulfated β-CD (7SβCD) having sulfate esters solely on the 6-positions at the narrow end of the bucket-shaped cyclodextrin molecule. This synthetic scheme was designed to retain the geometry of the cavity and the complexation properties of native β-cyclodextrin. Stalcup and co-workers [Stalcup, A., et al., *Anal. Chem.*, 68:1360–1368 (1996); Wu, W., et al., *Chromatogr.*, 18:1289–1315 (1995)] recently reported the use of a mixture of cyclodextrin sulfate esters for the separation of racemates of neutral compounds and amines in untreated fused-silica capillary, which was effective for 40 compounds investigated.

Despite these encouraging results, there is no universal system tor carrying out chiral separations by CE. This is because the CE separations are very dependent upon the extent of complexation with a particular cyclodextrin. In addition to the size of the CD cavity, interactions between the solute and the functional groups on the rim of the CD may influence chiral selectivity. Accordingly, the selection of a particular charged or neutral cyclodextrin best suited for the separation of a particular chiral pair remains an empirical process of trial and error.

For the foregoing reasons there is a need for novel set of charged cyclodextrins that can be used to resolve a broad range of chiral compounds by capillary electrophoresis. Ideally, the novel cyclodextrins can be synthesized using a simple procedure and give reproducible separations of enantiomers.

SUMMARY OF THE INVENTION

The present invention is directed to a set of charged cyclodextrins that satisfy the need to separate a broad range of chiral compounds by capillary electrophoresis. The preferred chiral selectors are highly sulfated α-, β-, and γ-cyclodextrins. These charged cyclodextrins have a higher degree of sulfation and narrower heterogeneity than commercially available cyclodextrins. CE analyses using highly sulfated cyclodextrins can improve the resolution of a wide variety of chiral drugs compared to other chiral selectors. Moreover, highly sulfated α-, β-, and γ-cyclodextrins produce separations which complement each other, permitting the resolution of an even broader range of neutral and basic drugs.

The charged cyclodextrins of the present invention can be an α-cyclodextrin, a β-cyclodextrin, or a γ-cyclodextrin having at least one hydrogen of a secondary hydroxyl replaced with a charged substituent. Preferred charged cyclodextrins have the following general formula:

For a cyclodextrin in which n is 6 or 8, at least about one $R^1$ group is a modified hydroxyl, and less than about n $R^1$ groups are hydroxyl. For a cyclodextrin in which n is 7, at least about 5 $R^1$ groups are modified hydroxyls, and less than about 3 $R^1$ groups are hydroxyl. The hydrogen of a modified hydroxyl is preferably replaced by a sulfate, carboxylate, phosphate, or a quaternary amine substituent. The most preferred substituent is sulfate.

Preferred highly sulfated alpha cyclodextrins possess at least about 7 sulfate substituents; preferred highly sulfated beta cyclodextrins possess at least about 12 sulfate substituents; and preferred highly sulfated gamma cyclodextrins possess at least about 9 sulfate substituents.

The charged cyclodextrins of the present invention can be used in a method of separating enantiomers of a small molecule by capillary electrophoresis. The method includes the steps of: a) filling a capillary with an electrophoresis buffer, which includes a charged cyclodextrin and an electrolyte; b) injecting a sample containing enantiomers of a chiral compound into the capillary; c) conducting an electrophoretic separation of the enantiomers; and d) detecting the enantiomers of the chiral compound. Preferably, the electrophoretic separation is conducted under conditions suppressing electroendoosmotic flow. For example, a coated capillary may be used or the electrophoresis buffer may be acidic. The sample is generally a small chiral molecule (MW<5,000), which is preferably a neutral or basic compound. Optionally, an internal standard, such as a salt of 1,3,6,8-pyrenetetrasulfonic acid, is added to the sample to allow normalization with respect to time.

The reagents of the present invention may be conveniently assembled into a kit for use in separating chiral compounds by capillary electrophoresis. The kits will contain at least two highly sulfated cyclodextrins selected from the group consisting of: a) an alpha cyclodextrin possessing at least about 7 sulfate substituents; b) a beta cyclodextrin possessing at least about 12 sulfate substituents; and c) a gamma cyclodextrin possessing at least about 9 sulfate substituents. In addition, the kits may optionally contain an electrophoresis buffer, a pH adjusting agent, an internal standard, and/or a capillary tube.

BRIEF DESCRIPTION OF THE DRAWINGS

These and other features, aspects, and advantages of the present invention will become better understood with regard to the following description, appended claims, and accompanying drawings where:

FIG. 1 shows electropherograms of 7SβCD (A), HSαCD (B), and a mixture of 7SβCD and HSαCD;

FIG. 2 shows electropherograms of 7SβCD (A), HSβCD (B), and a mixture of 7SβCD and HSβCD;

FIG. 3 shows electropherograms of 7SβCD (A), HSγCD (B), and a mixture of 7SβCD and HSγCD;

FIG. 4 shows electropherograms of some charged cyclodextrins, including ABI SBECD (A), and the sulfated cyclodextrins of Cerestar (B), and Aldrich (C);

FIG. 5 shows the electrophoretic separations of amphetamine obtained using HSαCD (A), HSβCD (B), and HSγCD (C); and FIG. 6 shows the electrophoretic separations of racemic thalidomide obtained using HSαCD (A), HSβCD (B), and HSγCD (C).

DETAILED DESCRIPTION OF THE INVENTION

The methods and reagents described herein entail a simple generalized procedure for separating enantiomers of neutral and basic drugs. A novel set of charged cyclodextrins that can serve as "hosts" to a broad range chiral molecule "guests" are used to differentiate between enantiomer pairs. Differential complexation with the enantiomers results in altered electrophoretic mobilities and separation of the pair during capillary electrophoresis.

CD's are rings of oligosaccharides, composed of glucose units connected to each other through α(1,4)-glycosidic bonds. Although CDs from 6 up to 12 glucose units have been isolated, those with six, seven, and eight units, termed α-, β-, and γ-CD respectively, are preferred. The CD's shape is similar to that of a truncated cone, with a relatively hydrophobic cavity that is able to host analytes. Native CD's have an hydrophilic outside region, which has hydroxyl groups at the 2, 3, and 6 positions of the glucopyranose molecules.

The CD's of the present invention have modified hydroxyls comprising a charged substituent at the 6-position of each glucose unit on the cyclodextrin. In addition, at least one of the secondary hydroxyls at the 2- and/or 3-positions (most likely at the 2-position), are also substituted with a charged group. This means that in addition to having charged groups at the narrower openina of the truncated cone, charged groups also occur at the rim of the wider opening of the cyclodextrin bucket. Since the wider rim is the part that wraps around the "guest" molecule during complexation, the receiving end of the bucket is perturbed relative to that of native cyclodextrin. This perturbation of the bucket, due to the alteration of the secondary hydroxyls, has proven beneficial to the selective complexation process and unexpectedly results in better chiral discrimination by CE.

The structural formula for preferred versions of the HSCD is as follows:

For a cyclodextrin in which n is 6 or 8, at least about one $R^1$ group is a modified hydroxyl, and less than about n $R^1$ groups are hydroxyl. For a cyclodextrin in which n is 7, at least about 5 $R^1$ groups are modified hydroxyls, and less than about 3 $R^1$ groups are hydroxyl. The charged substituent, which modifies the hydroxyl groups, is preferably negatively charged, for example, a carboxylate, phosphate, or sulfate group. Alternatively, the substituent can be positively charged, for example, with a quaternary amine. The most preferred substituent is a sulfate group.

For α-CD's, at least about 7 hydroxyl groups are substituted, and preferably about 10 to 12 are substituted. A most preferred α-CD has about 11 hydroxyl groups modified with sulfate substituents.

For β-CDs, at least about 12 hydroxyl groups of the CD are modified with a charged substituent, and preferably about 12 to 15 are substituted. A most preferred β-CD has about 12 hydroxyl groups modified with sulfate substituents.

For γ-CD's, at least about 9 hydroxyl groups are substituted, and preferably about 12 to 16 are substituted. A most preferred γ-CD has about 13 hydroxyl groups modified with sulfate substituents.

Synthesis of the preferred sulfated CD's involves a reaction between dried α-, β-, or γ-cyclodextrin and 19 molar equivalents of sulfur trioxide-trimethylamine complex in DMF without any protection of functional groups. This reaction consistently produces a cyclodextrin with a high degree of sulfation. Accordingly, the product of this synthesis is called Highly Sulfated α-, β-, or γ-Cyclodextrins (HSαCD, HSβCD, or HSγCD, respectively).

Any of a wide variety of analytes may be evaluated in accordance with the present inventions. Suitable analytes can include any "guest," e.g., optical isomers, enantiomer pairs, racemic drug mixtures, which can form a complex with a charged CD "host." Virtually any chiral pair having different complexation equilibrium constants with the charged CDs can be analyzed as described herein. The samples will generally be small molecules (MW<5,000) having an optically active chiral center. In preferred embodiments of the present invention, the samples are pharmaceutical compounds, such as those listed in the examples of the present application. The most preferred samples are neutral compounds or amines.

At least one internal marker may be added to the sample to allow normalization with respect to time. Preferably the marker migrates ahead of the assay constituents providing a time zero starting point for comparing the relative migration times of the enantiomers. Pyrene-1,3,6,8-tetrasulfonate (PTS) tetrasodium salt is a preferred internal standard, which can serve as a reliable marker for most separations. Under acidic conditions, PTS produces a peak with short migration time that is primarily dependent only on its electrophoretic mobility. Due to its large molecular size and its four negative charges, it has no interaction with the sulfated cyclodextrins.

In accordance with the present invention, capillary electrophoresis (CE) is used to mediate the separation of the chiral compounds. In general, CE involves introduction of sample constituents into a capillary tube, i.e., a tube having an internal diameter of from about 2 to 2,000 microns (μm), and the application of an electric field to the tube. The electric potential of the field both pulls the assay constituents through the tube and separates them according to their individual electrophoretic mobilities.

The CE method of the present invention is preferably conducted under conditions that suppress electroendoosmotic flow (EOF). When using an "open" CE format, a fused silica capillary tube is filled with an electrically conductive buffer devoid of polymer and gel. The fused silica capillary becomes significantly negatively charged at a pH greater than about 5.0, which attracts a layer of positive ions from the buffer. As these ions flow towards the cathode, under the influence of the electric potential, the buffer solution and the sample being analyzed are carried along in the same direction. The resulting EOF provides a fixed velocity component, which pushes both neutral species and ionic species, regardless of charge, towards the cathode. Thus, under conditions which do not suppress electroendoosmotic flow, the migration rate of the sample constituents is primarily determined by the underlying EOF, which can overwhelm the electrophoretic mobilities of the sample constituents.

There are a number of methods that can suppress the EOF enough to give separations based primarily on the electrophoretic mobilities of the sample constituents. The simplest approach is the use of electrophoresis buffers having an acidic pH. Accordingly, the preferred buffers of the present invention have a pH of less than about 7. Most preferred buffers have a pH range of about 1 to about 5, which for most applications is optimized at about pH 2.5 to 4.

An electrolyte having a suitable buffering capacity within the preferred pH range is included as a component of the electrophoresis buffer. Suitable electrolytes for use at an acidic pH include organic or inorganic phosphate, acetate, or citrate. A preferred electrolyte of the electrophoresis buffer is triethylammonium phosphate. The molarity of the electrolyte in the buffer is generally about 5 to 200 mM, preferably 10 to 100 mM, and most preferably about 25 to 50 mM. The ionic strength of buffers having higher concentrations of electrolytes may give rise to undesirable Joule heating effects.

An alternative method for suppressing EOF is the use of coated capillary tubes. The surface of the capillary can be coated dynamically by including additives such as surfactants, zwitterionic salts, or hydrophilic linear polymers to the buffer system. However, a preferred capillary coating would be a polymer, such as a polyacrylamide, polyethylene glycol, or diol-epoxy coating, chemically bonded to the capillary surface. A most preferred polymer coating is poly (vinyl alcohol), known simply as PVA.

The capillary tubes used in the practice of the invention generally have an internal diameter, which ranges in size from about 10 μm to about 200 μm. Most preferably, capillary tubes with an internal diameter of about 25 μm are used for CE separation of enantiomers. The preferred length of the capillary tube is from about 10 to about 100 cm, most preferably about 27 cm. A detection window is preferably located in the capillary tube approximately 6.5 cm from the column outlet.

Figure 4A:
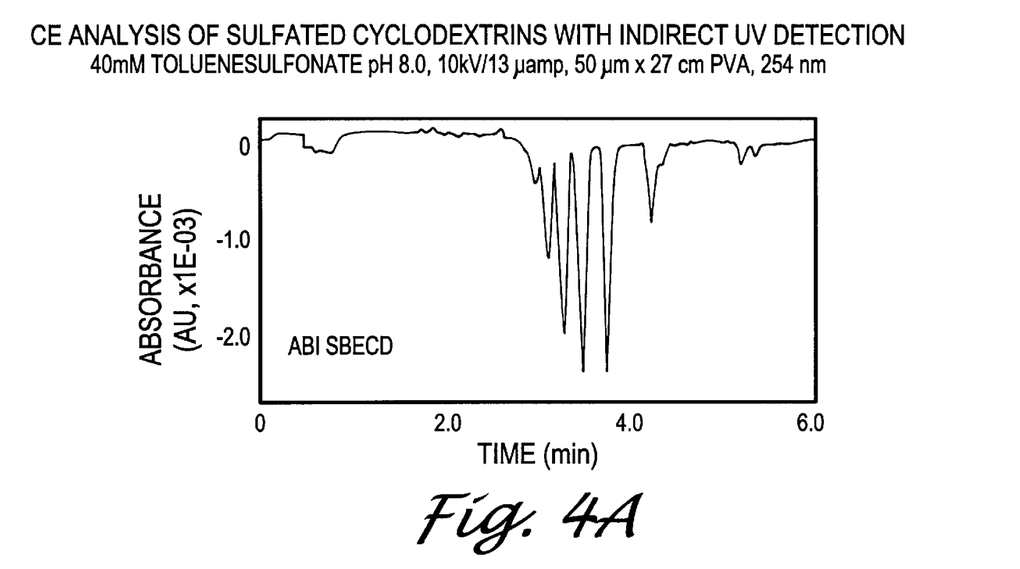
Figure 4B:
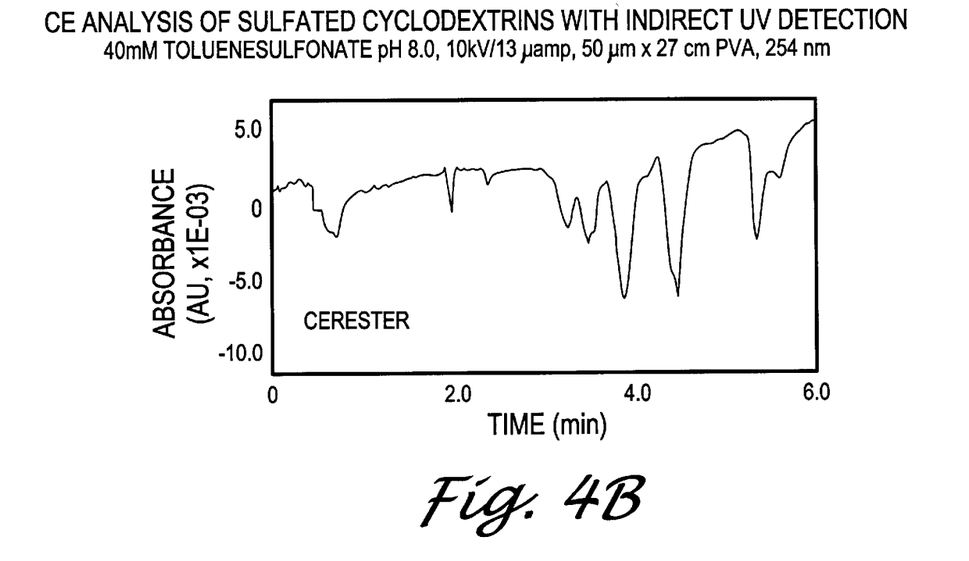
Figure 4C:
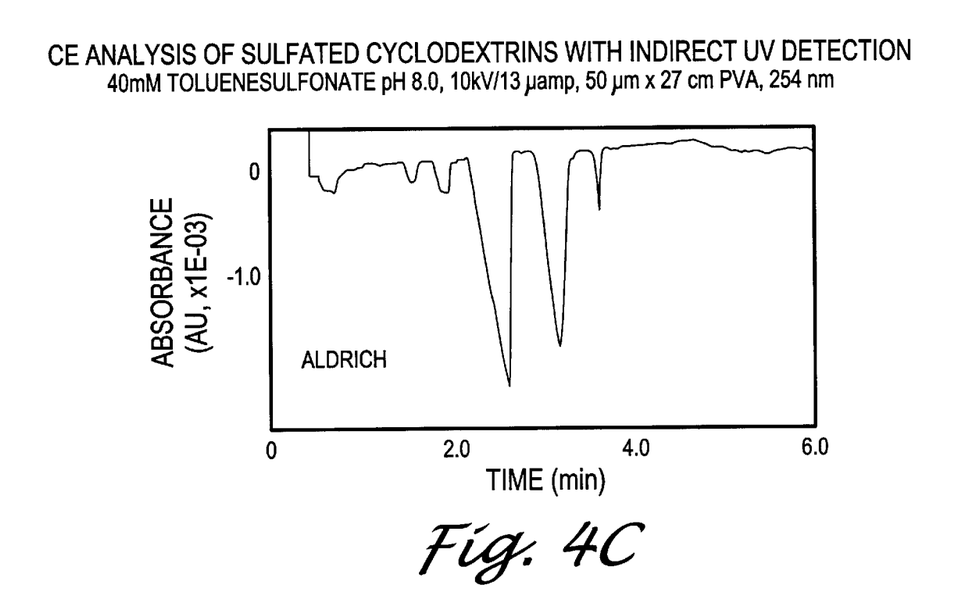
Figure 5A:
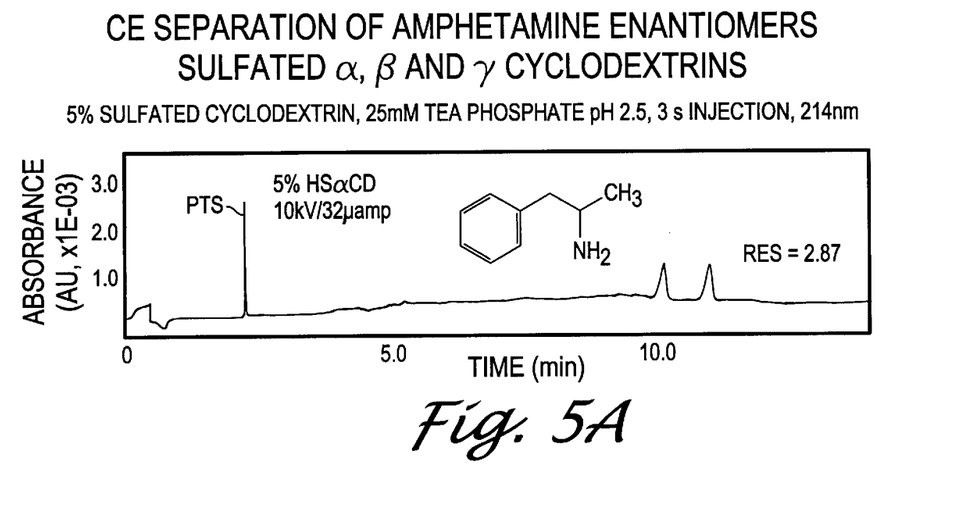
Figure 5B:
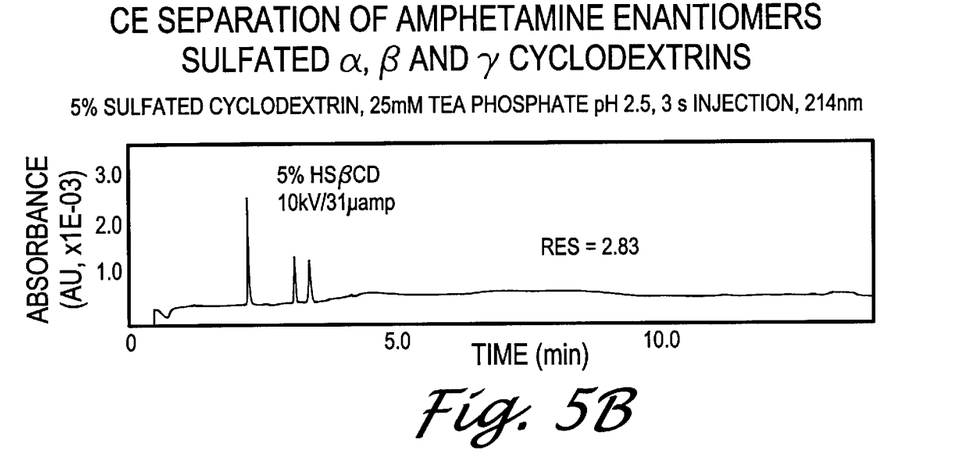
Figure 5C:
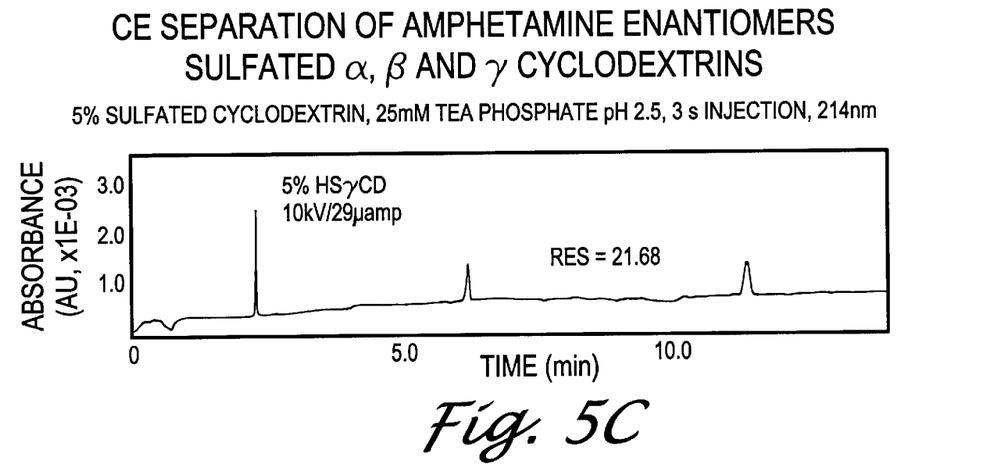

The selection of an α-, β-, or γ-cyclodextrin "host" for use with a particular analyte "guest" is generally an empirical matter. A rough guide for the choice of CD derivatives is that separation with α-CD is preferred for compounds with one aromatic ring, β-CD is preferred for compounds with a substituted aromatic ring, and γ-CD is preferred for compounds with multiple rings. However, as shown in FIGS. 4 and 5, actual results may deviate materially from this general rule of thumb.

Similarly, the concentration of charged α-, β-, or γ-cyclodextrin within the capillary during electrophoretic separation is can be optimized in an empirical manner for each chiral compound. In general, the concentration of the charged cyclodextrin should be in molar excess relative to the sample constituents. A suitable CD concentration range for optimization is between about 1% to about 20%, preferably narrowed to about 2% to about 10%. The most preferred concentration of charged CD is about 5%.

The CD's are preferably added to the electrophoresis buffer and introduced into the capillary tube. A separation buffer can be prepared by mixing 1 part 20% HSCD in water, 2 parts of a 2× solution of electrophoresis buffer (e.g. 50 mM trethylammonium phosphate, pH 2.5), and 1 part water. The capillary is rinsed with the separation buffer for 1 min by pressure at 20 psi. After sample injection, the capillary inlet and outlet are immersed in the separation buffer and voltage is then applied to initiate electrophoresis. Less preferred alternatives include binding the CD's to the capillary wall or including the CD's in a gel matrix.

Samples are prepared by dissolving an analyte in 0 to 50% methanol in water at a detectable concentration, generally about 0.1 to 10 mM and preferably about 1 mM. In addition, an internal standard, such as PTS, may be added to the sample at a concentration about half that of the analyte, preferably about 0.5 mM. The sample can then be introduced by electrokinetic injection, hydrodynamic pressure, vacuum or syringe pump. Preferably, samples are introduced into the capillary column by pressure injection, at pressures ranging from 0.5 to about 15 psi, most preferably about 0.5 psi, and during a period from about 1 to 99 sec, most preferably about 2 to 5 sec.

A P/ACE 2000 series, P/ACE 5000 series or P/ACE MDQ Capillary Electrophoresis Systems (Beckman Instruments, Inc., Fullerton, Calif.). In addition Beckman System Gold™ software, Beckman P/ACE™ software, or the Beckman P/ACE™ Station software controlled by an IBM PS/2, IBM 350 466 DX2 or IBM 350-P90 PC, may be used in the practice of the invention. The sample is subjected to electrophoresis at a voltage ranging from 1 kV to about 100 kV, preferably 5 kV to about 20 kV, and most preferably about 7.5 kV to about 12 kV.

Detection is preferably conducted by UV absorbance, preferably at a wavelength that detects the sample constituent and internal standard, but not the charged CD. Preferred wavelengths for detection range from about 180 nm to about 380 nm, with a most preferred detection wavelength of about 214 nm.

When CE is conducted under conditions that suppress electroendoosmotic flow, e.g., at an acidic pH, CE is preferably run using reversed polarity, with the anode placed nearest to the detection window. Under these conditions the analytes are dragged to the anode by complexation with a negatively charged cyclodextrin migrating towards the anode. However, if the tail of a faster migrating major peak obscures a minor peak, it may be desirable to reverse the migration order of the peaks. In general, the favored separation condition is one where a minor contaminant migrates ahead of the principal component. Reversal of the migration order can be accomplished by elevating the pH of the buffer to greater than about 7, preferably about pH 8, and changing the polarity so that the cathode is nearest to the detection window. Under such conditions, the EOF is strong enough to sweep all compounds to the cathode, including the free and analyte-bound charged cyclodextrins.

In order to facilitate a systematic scheme for optimizing chiral analysis by CE, the reagents of the present invention may be conveniently assembled into a kit. To aid in selecting the most suitable cyclodextrin "host", the kits will contain at least two highly sulfated cyclodextrins selected from the group consisting of: a) an alpha cyclodextrin possessing at least about 7 sulfate substituents; b) a beta cyclodextrin possessing at least about 12 sulfate substituents; and c) a gamma cyclodextrin possessing at least about 9 sulfate substituents.

In addition, the kits may optionally contain at least one electrophoresis buffer, preferably at an acidic pH. However, another buffer for use at a higher pH may be included, as well as a pH adjusting agent, such as NaOH or phosphoric acid. Altering the composition and/or pH of the buffer may improve resolution and/or reverse the migration order of the chiral pair undergoing analysis. Further additions to the kit can include an internal standard, such as PTS, and coated or uncoated capillary tubes.

The previously described versions of the invention have many advantages, including a simple one-step method of synthesis, reproducible separations of a wide variety of optical isomers, and improved resolution for a number of neutral and basic chiral compounds. The method is inexpensive and versatile compared to the methods of chiral analysis that use HPLC, which requires a number of different stationary phase columns to optimize performance. The reagents, methods, and kits of the present invention can be readily adapted to a system of quality control to monitor the stereochemical purity of pharmaceutical drugs, food nutrients, environmental pollutants, pesticides, or any other racemic mixture.

The materials and methods of the present invention may be better understood by reference to ithe following examples.

EXAMPLE 1

Synthesis of HSCDs

This first set of examples demonstrates the simple single step methods that can be used to synthesize sulfated α-, β-, or γ-cyclodextrins, as well as the consistent high degree of sulfation of the resulting products.

Synthesis of a highly sulfated α-cyclodextrin was conducted by adding 100 grams of oven-dried α-cyclodextrin (102.8 mmol) and 900 ml of anhydrous dimethylformarnide (DMF) to a dried 2-L reactor equipped with a mechanical stirrer. The vessel was heated in an oil bath at 50° C. with stirring to dissolve most of the solid. A partially dissolved mixture of sulfur trioxide trimethylamine complex (272 g, 1,953 mmol) in 300 ml of DMF was slowly poured into the reactor and stirred vigorously at 50° C. A gummy product was formed after 35 min and the stirring was interrupted. After cooling to room temperature solvent was decanted, the gummy product was rinsed twice with 300 ml of reagent alcohol, and the solvent was again decanted.

Similarly, synthesis of a highly sulfated β-cyclodextrin was conducted by adding 100 grams of oven-dried β-cyclodextrin (88.1 mmol) and 500 ml of anhydrous dirnethylformamide (DMF) to a dried 2-L reactor equipped with a mechanical stirrer. The vessel was heated in an oil bath at 50° C. with stirring to dissolve most of the solid. A partially dissolved mixture of sulfur trioxide trimethylamine complex (240 g, 1,724 mmol) in 300 ml of DMF was slowly poured into the reactor and stirred vigorously for 1 h at 50° C. A gummy product was formed and the stirring was interrupted. Solvent was decanted while hot, the gummy product was rinsed twice with 300 ml of reagent alcohol, and the solvent was again decanted.

An analogous synthetic scheme for producing a highly sulfated γ-cyclodextrin was conducted by adding 100 grams of oven-dried γ-cyclodextrin (77.1 mmol) and 900 ml of anhydrous dimethylformamide (DMF) to a dried 2-L reactor equipped with a mechanical stirrer. The vessel was heated in an oil bath at 50° C. with stirring to dissolve most of the solid. A partially dissolved mixture of sulfur trioxide trimethylamine complex (204 g, 1,460 mmol) in 300 ml of DMF was slowly poured into the reactor and stirred vigorously at 50° C. A gummy product was formed after 35 min and the stirring was interrupted. After cooling to room temperature solvent was decanted, the gummy product was rinsed twice with 300 ml of reagent alcohol, and the solvent was again decanted.

The gummy products, from the synthetic schemes described above, were dissolved in 375 ml of 4 N sodium hydroxide and stirred. The solutions were maintained at a pH of about 10, transferred to 2-L round bottom flasks, and subjected to rotary evaporation to remove the trimethylamine, as well as some water, under reduced pressure. The flasks were then placed in a cold room overnight. Solids from the remaining solutions (about 600 ml) were collected by filtration. About 800 ml of acetone was added to each of the filtrates and each formed a soft gum. The mixtures were stirred vigorously for 10 min and the acetone was decanted. Another 800 ml of acetone was then added, stirred for 10 min, and decanted. The gummy products were each dissolved in 500 ml of deionized water and the solutions were slowly poured into 2 L methanol with vigorous stirring. The resultant off-white solids were collected via filtration, washed three times with 300 ml of methanol, and dried at 110° C. under high vacuum overnight.

When resuspended in water, solutions of all HSCD had a light brown color due to an impurity which originated from the sulfur trioxide-trimethylamine complex. The solutions were easily decolorized by treatment with decolorizing activated carbon (Aldrich Cat. No. 16,155-1) and then clarified by centrifugation and filtration through a 0.45 $\mu$m syringe filter.

Four different lots of HSβCD, one lot of HSαCD, and one lot of HSγCD were subjected to elemental analysis and compared to a lot of 7SβCD, synthesized according to the methods of Moriya et al., as adapted by Vincent et al. The degree of sulfation was determined for each lot, as summarized in Table 1.

TABLE 1

Sulfation of Cyclodextrins

| Cyclodextrin | Degree of Sulfation | Sulfate per Glucose |
|---|---|---|
| HSαCD | 11.10 | 1.85 |
| HSβCD | | |
| GS4747-65ND | 12.50 | 1.78 |
| GS4747-65 | 12.20 | 1.74 |
| GS4747-85 | 12.04 | 1.72 |
| GS4747-90 | 12.35 | 1.76 |
| HSγCD | 12.9 | 1.61 |
| 7SβCD | 7.24 | 1.03 |

As shown in Table 1, the synthetic procedure used to produce HSCDs of the present invention consistently gave a high degree sulfation (>11), with an average of at least about 1.6 sulfate molecules per glucose molecule.

EXAMPLE 2

Characterization of Sulfated-β-CDs by Indirect UV Detection

This example shows the HSCDs of the present invention are more highly sulfated than the sulfated CD of Vincent et al. and less heterogeneous than several commercially available sulfated CDs.

Sulfobutyl ether β-cyclodextrins (SBE-βOCD) were purchased from Perkin-Elmer/ABI (Foster City, Calif.) with an average degree of sulfation of 4 per cyclodextrin. In addition, Cerestar (Hammond, Ind.) provided a mixture of sulfated β-CD's (average degree of sulfate =4) and sulfated cyclodextrin with an average degree of sulfation of 7 to 10 per β-CD was obtained from Aldrich (Milwaukee, Wis.). These commercially available charged CD's were compared with a C-6 sulfate ester of b-cyclodextrin (7SPCD, 7 sulfate groups per b-CD) of Vincent et al. and α-,β-, and γ-HSCDs synthesized according to Example 1.

CE analysis with indirect UV detection was performed on a P/ACE 5000 CE system by Beckman Instruments Inc. (Fullerton, Calif.), equipped with a UV detection at 254 nm using a 50 $\mu$m×27 cm PVA-covalently coated-capillary obtained from Beckman Instruments Inc. U.S. Pat No. 2,232,111). The separation buffer was composed of 40 mM p-toluenesulfonic (TSA) acid adjusted with Tris to pH 8.0. In this method, the non-absorbing sulfated cyclodextrins displace the ionic chromophore, TSA, which migrates electrophoretically to the anode to produce zones of lower UV absorbance. The result is that the anionic analytes produce signals of negative absorbance as they pass the detector. The peaks are broader than those obtained with direct UV absorbance detection presumably due to an imperfect match of mobilities between the sulfated cyclodextrin analytes and the TSA background chromophore.

Figure 1A:
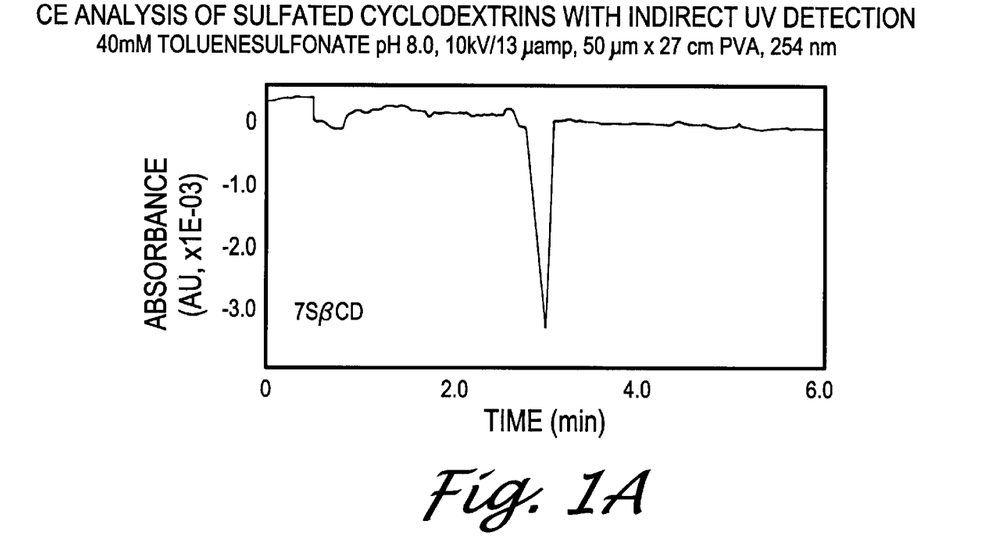
Figure 1B:
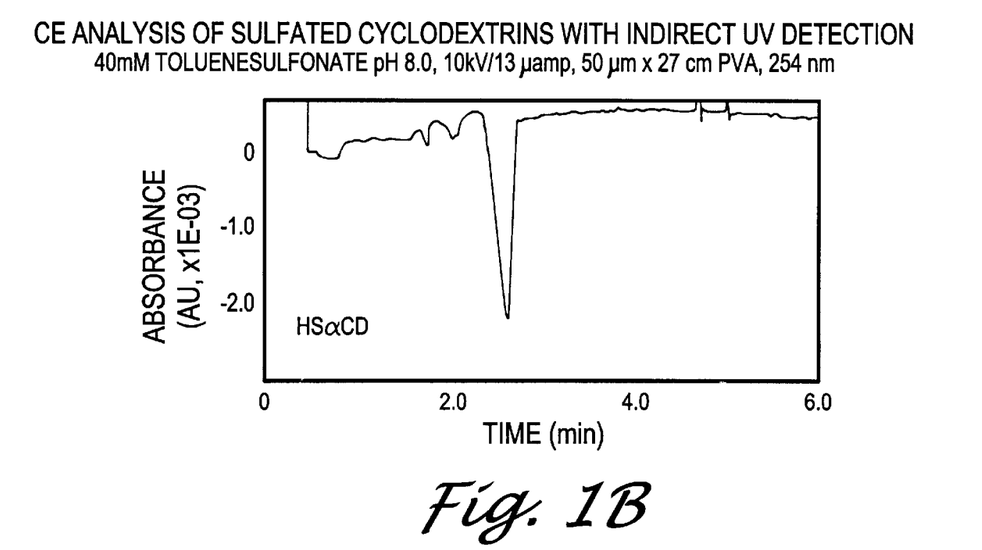
Figure 1C:
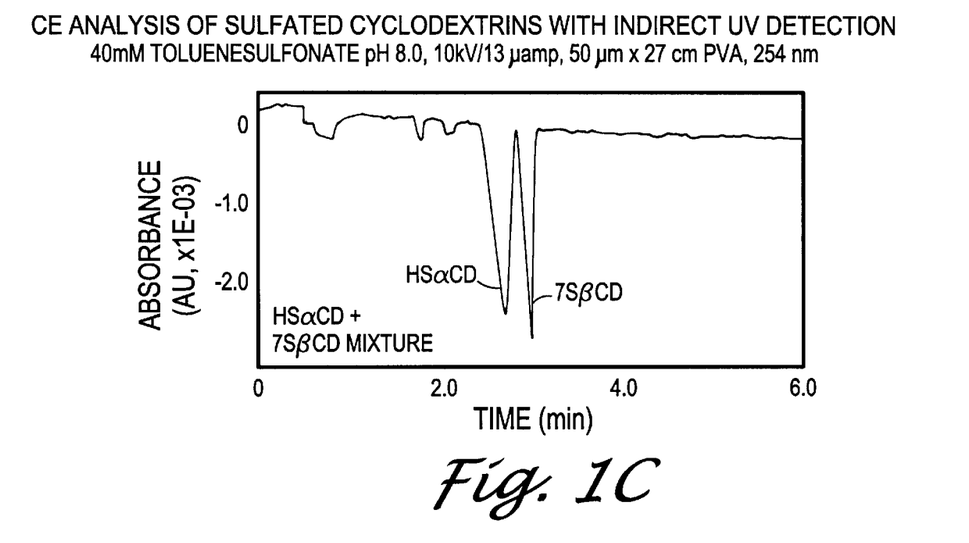
Figure 2A:
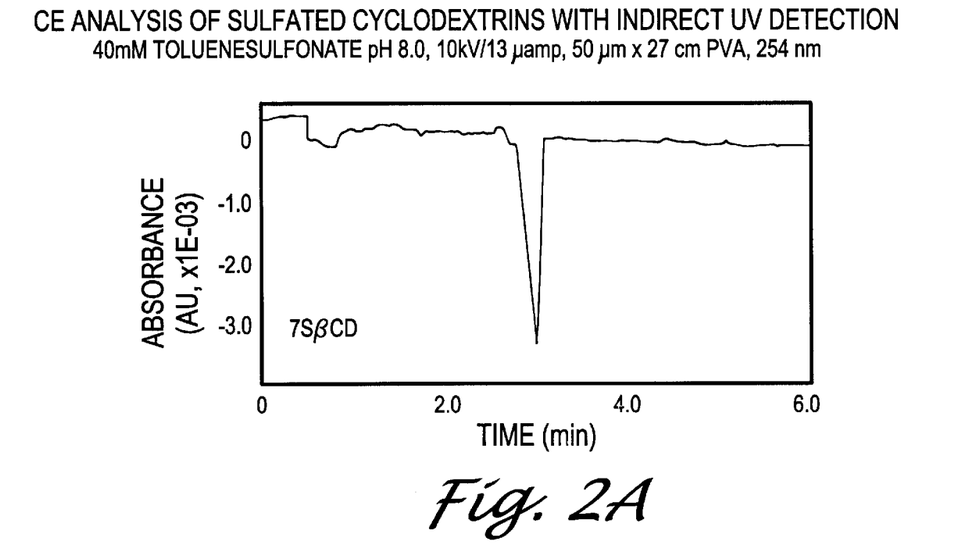
Figure 2B:
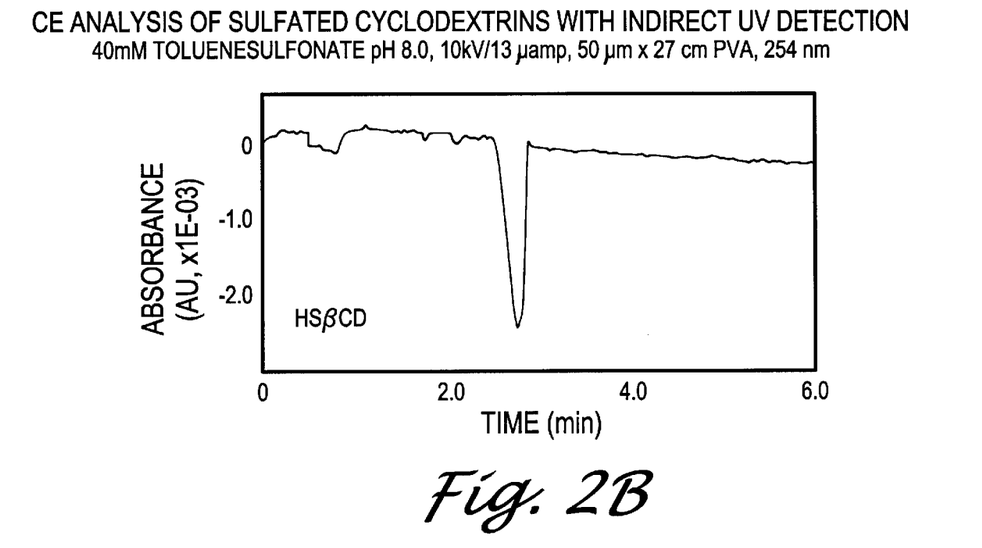
Figure 2C:
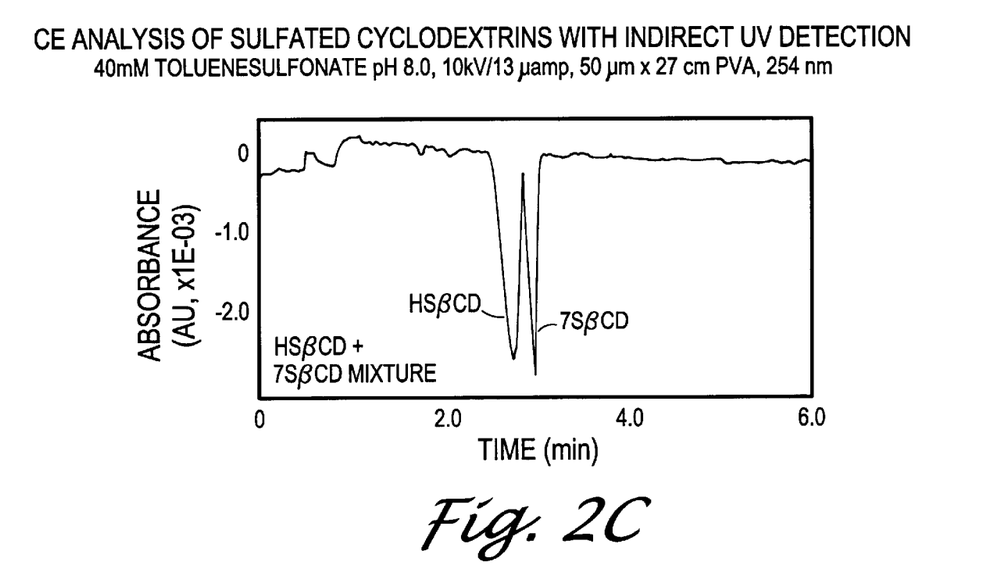
Figure 3A:
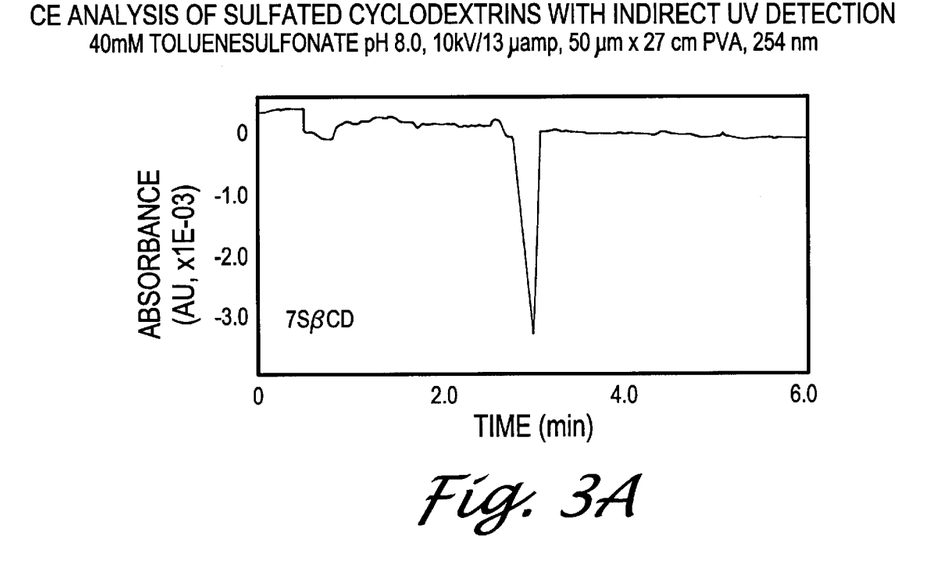
Figure 3B:
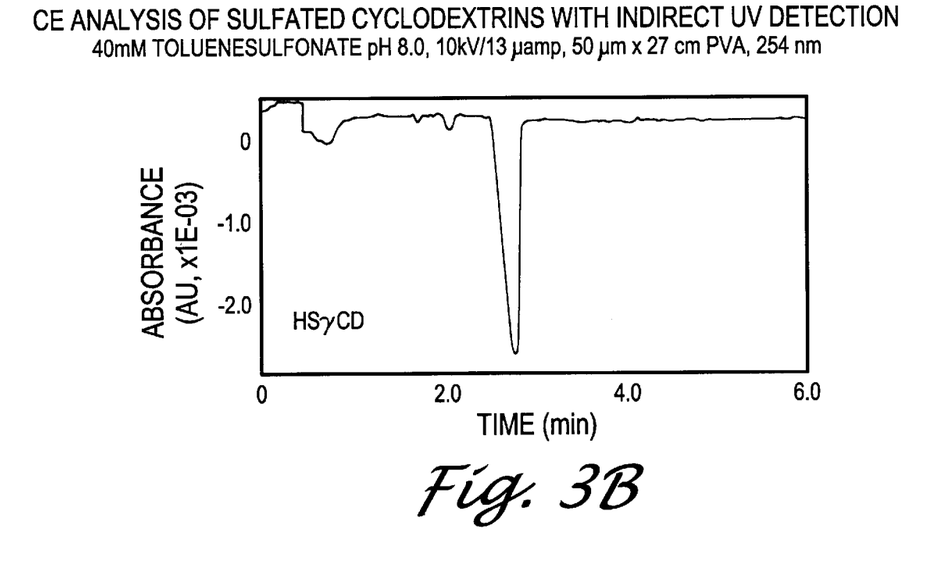
Figure 3C:
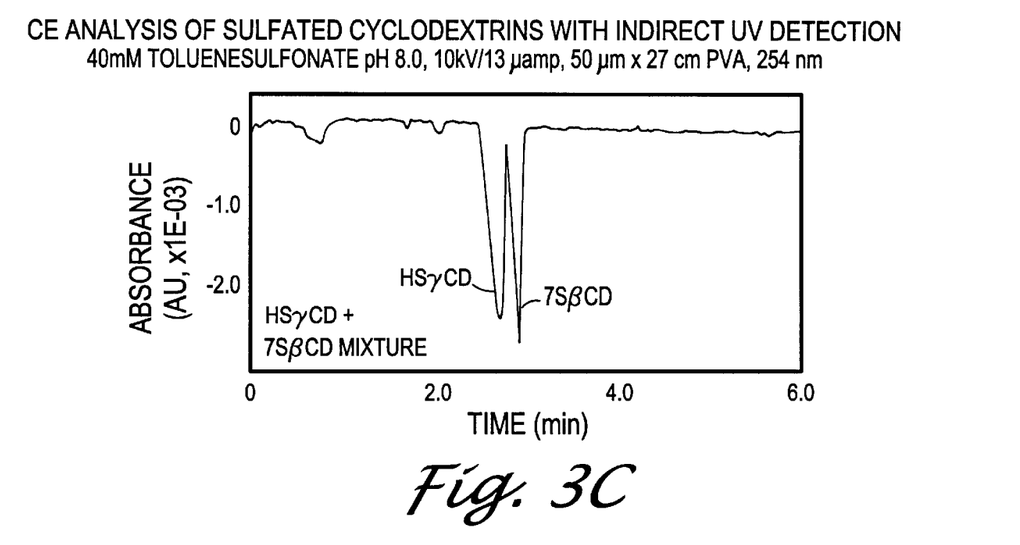

The resulting electropherograms for HSαCD, HSβCD, and HSγCD are shown in FIGS. 1, 2, and 3, respectively. All the α-, β-, and γ-HSCDs produce peaks with shorter migration times than 7SβCD, indicating that the degree of sulfation is higher than seven for each HSCD. The fact that mixtures of an HSCD and 7SβCD produce two distinct peaks is an indication that the Beckman HSCDs are not gross mixtures of completely random-sulfated species. Moreover, if the mixtures contained HSCD molecules with 8, 9, or 10 sulfates, the expected electropherograms would not display distinct separations between the HSCD and 7SβCD peaks. Accordingly, the results confirm that the average degree of sulfation of the HSCD's is greater than 10.

The fact that the peaks of the HSCDs are not much wider than that of the 7SβCD indicates that the molecular heterogeneity of the HSCDs is not broad. In comparison, the electropherograms of the SBE-βCD, Cerestar sulfate cyclodextrin, and Aldrich sulfated β-CD (FIG. 4) are much more complicated, consisting of several distinct peaks. By comparison, the HSCD is a mixture of cyclodextrins with higher degree of sulfation and narrower heterogeneity than that of the other commercially available sulfated cyclodextrins.

EXAMPLE 3

Chiral Separations Using the Highly Sulfated β-Cyclodextrin (HSβCD)

The most important factor in the selection of a chiral selector for CE is its ability to resolve the widest variety of analytes. Accordingly, we conducted a comparative study to show that enantioseparation of neutral and basic drugs using HSβCD compares favorably with chiral separations using SBECD from ABI (average of 4 sulfobutyl ether group per β-CD), sulfated β-CDs from Cerestar, (variable number of sulfate groups per β-CD), and the C-6 sulfate ester of β-cyclodextrin (7SβCD, 7 sulfate groups per β-CD) of Vincent et al.

Phosphate buffers were prepared by titrating phosphoric acid with the corresponding base, such as triethylamine or NaOH solution. Sulfated-βCD was dissolved in 25 mM triethylammonium phosphate, pH 2.5. Due to the inexact nature of sulfate content, concentration of the sulfated-βCDs were expressed in weight per volume basis. Samples of neutral racemates were dissolved in 50% methanol in water while the amino-based racemates were dissolved in water. All samples injected into the capillary contained 1 mM of the racemic mixture and 0.5 mM 1,3,6,8-pyrenetetrasulfonic acid sodium salt (PTS) as internal standard. PTS migrated ahead of any compound in the mixture because of its four negative charges.

A large number of racemates of neutral compounds and amines were subjected to capillary electrophoresis under virtually the same separation conditions. Separations were performed on a P/ACE 5000 CE system by Beckman Instruments Inc. (Fullerton, Calif.), equipped with UV detection at 214 nm using a 25 μm×27 cm untreated fused-silica capillary. The concentrations of the sulfated cyclodextrins were varied (see Tables 2A and 2B). Electrophoresis was conducted at 10 or 12 kV applied voltage under conditions of reversed polarity. The results are summarized in Tables 2A and 2B. The percent values, shown in parentheses, indicate the concentration of sulfated cyclodextrin in the separation buffers that produced optimum separations.

TABLE 2A

Resolution of Neutral Chiral Racemic Mixtures
(Varying concentrations of sulfated β-cyclodextrin)

| Neutral Compounds | HSβCD | 7SβCD | Cerestar | ABI SBECD |
|---|---|---|---|---|
| Thalidomide | 3.28(5%) | 0.59(2%) | | 1.28(5 mM) |
| Warfarin | 3.11(5%) | 2.50(5%) | 0.79(20%) | 0.78 (0.5 mM) |
| Glutethimide | 7.94(5%) | 0.00(5%) | | |
| Lorazepam | 20.85(5%) | 1.93(5%) | | |
| Chlorthalidone | 1.48(5%) | 3.52(5%) | | |
| Praziquantel | 11.8(5%) | 0.49(5%) | | |
| 5-(4-Methyl-phenyl)-phenylhydantoin | 2.37(5%) | 0.71(5%) | 0.74(5%) | 1.81 (0.5 mM) |
| α-Methyl-α-phenylsuccinimide | 3.31(5%) | 1.07(5%) | 0.67(20%) | 1.11(2 mM) |
| Benzoin | 2.53(5%) | 2.18(5%) | 0.56(2%) | 1.18(2 mM) |
| α-Cyclopropylbenzyl alcohol | 8.27(5%) | 4.48(2%) | | |
| 2,2-Dimethyl-1-phenyl-1-propanol | 1.23(5%) | 0.00 (2–10%) | | |
| 1,2-Diphenyl-2-propanol | 1.40(5%) | 0.00 (2–10%) | | |
| Hydrobenzoin | 20.14(5%) | 5.62(2%) | | |
| 2-Phenylcyclohexanone | 1.90(5%) | 0.00 (2–10%) | | |
| 1,2,3,4-Tetrahydro-1-napthol | 1.86(5%) | 0.77(5%) | | |
| trans-2-Phenylcyclohexanol | 3.22(5%) | 0.00(5%) | | |
| 9-methyl-Δ$^{5,10}$-octalin-1,6-dione | 3.51(5%) | 0.82(5%) | | |
| 1,1'-Bi-2-napthol | 11.85(5%) | 2.12(5%) | | |

TABLE 2B

Resolution of Basic Chiral Racemic Mixtures
(Varying concentration of sulfated β-cyclodextrin)

| Amines | HSβCD | 7SβCD | ABI SBECD |
|---|---|---|---|
| Amphetamine | 2.62(5%) | 1.43(5%) | |
| Methamphetamine | 1.79(5%) | 2.00(5%) | |
| 3,4-Methylenedioxyamphetamine | 1.06(5%) | 1.14(5%) | |
| 3,4-Methylenedioxy-methamphetamine | 0.88(5%) | 1.20(5%) | |
| Ephedrine | 2.12(5%) | 5.58(5%) | |
| Terbutaline | 1.44(5%) | 2.77(5%) | 2.56(5 mM) |
| Metaproterenol | 1.00(5%) | 2.06(5%) | 2.56(5 mM) |
| Salbutamol | 6.19(5%) | No peaks | |
| Fluoxetine | 1.20(5%) | 0.26(5%) | |
| Verapamil | 1.17(5%) | 0.00(5%) | 0.80(1 mM) |
| Phenylpropanolamine | 2.69(5%) | 0.00(5%) | No peaks |
| Miconazole | 2.18(5%) | 3.54(5%) | 0.83(1 mM) |
| Phenylalanine | 8.88(5%) | 1.18(5%) | |

All of the amines and seven of the neutral compounds tested are known drugs. Two of the amines analyzed, fluoxetine and verapamil, were obtained from capsules of commercial drugs (Prozac® and Verelan®, respectively).

The results in Tables 2A and 2B show the resolution, R, of the peaks, which is defined as the quotient of the distance between the peak centers Δx and 4σ, the mean of the two standard deviations of the peaks. The results show that the HSβCD, which was prepared in a simple one-step synthesis, provided good resolution (>1) for 18 neutral racemates and 11 amine enantiomeric pairs. Some of the racemates (glutethimide, lorazepam, praziquantel, hydrobenzoin, α-cyclopropylbenzyl alcohol and 1,1'-bi-2-naphthol) produced unusually large resolution values (>7) using the HSβCD. By comparison, the 7SβCD produced adequate separation for a much lower number of chiral pairs (8 neutrals and 8 amines).

One observation from the electropherograms of the neutral racemates when using the HSβCD was that migration times were in general slower than the corresponding times for the 7SβCD separations. This suggests that the complexation equilibrium constant between the 7SβCD and most of the neutral compounds is higher than the corresponding values for HSβCD. This higher affinity is presumably the main reason that 7SβCD produced poor separations for a majority of the neutral compounds tested, i.e., the complex formation is too strong for both enantiomers resulting in no chiral discrimination.

For chiral amines, the opposite trend was observed. The migration times produced by HSβCD were almost all shorter than those obtained using the 7SβCD. One reason for this result is that the higher degree of sulfation of the HSβCD produces higher electrophoretic mobilities towards the anode due to more negative charges. It is likely that the increased negative charges also produced higher electrostatic attraction between the sulfated cyclodextrin and the protonated amines. Unlike the case of the neutral analytes where higher complexation constants appear to have produced lower resolution, the apparently higher-affinity of Beckman HSβCD for amines produced a larger number of successful chiral amine separations than the 7SβCD.

The results show large differences in the resolving power among the various charged CDs. Those CD's having an average degree of sulfation greater than 7 showed substantially better chiral resolution with wider range of molecular species (see Table 2A and 2B). In this regard, the HSβCD prepared using the simple, one-step, high-yield synthesis, described herein, compared favorably with any of the various sulfated cyclodextrins tested.

EXAMPLE 4

Effect of Different Synthesis Lots on Reproducibility of CE Separation

Another important criterion for a chiral selector is the reproducibility of performance among different synthesis lots. Since the direct sulfation of three different types of hydroxyls (2-, 3, and 6-positions on each glucose unit) was expected to produce a more random substitution than the five-step synthesis of the 7SβCD compound, variation within different lots of HSCD was a possibility that had to be considered. In view of this, the five different lots of HSCD (GS4747-65, GS4747-70, GS4747-82, GS4747-85 and GS4747-90) resulting from the five syntheses were tested for the separation of 5-(4-methylphenyl)-5-phenylhydantoin, α-methyl-α-phenylsuccinimide and thalidomide racemates. The results in Table 3 show that the reproducibility in migration time and resolution is very good for four of the synthetic lots. Only Lot 85 was somewhat different from the others, producing faster migration and lower resolution. These results show that repeated syntheses using the simple procedure of direct sulfation of unprotected β-HSCD yields a consistent product with reproducibly superior performance as chiral selector for CE.

TABLE 3

Reproducibility of Resolution Among Different β-HSCD Lots

| | Highly Sulfated β-Cyclodextrin Lot Number (GS4747-XX) | | | | |
|---|---|---|---|---|---|
| Enantiomers | 65 | 70 | 82 | 85 | 90 |
| 5-(4-Methylphenyl)-5-phenylhydantoin | 2.54 | 2.59 | 2.17 | 1.9 | 2.77 |
| α-Methyl-α-phenylsuccinimide | 3.41 | 3.35 | 3.67 | 2.07 | 3.68 |
| Thalidomide | 3.61 | 3.72 | 3.24 | 3.00 | 3.28 |

EXAMPLE 5

Chiral Separations Using Highly Sulfated α-, β-, and γ-Cyclodextrins

Figure 6A:
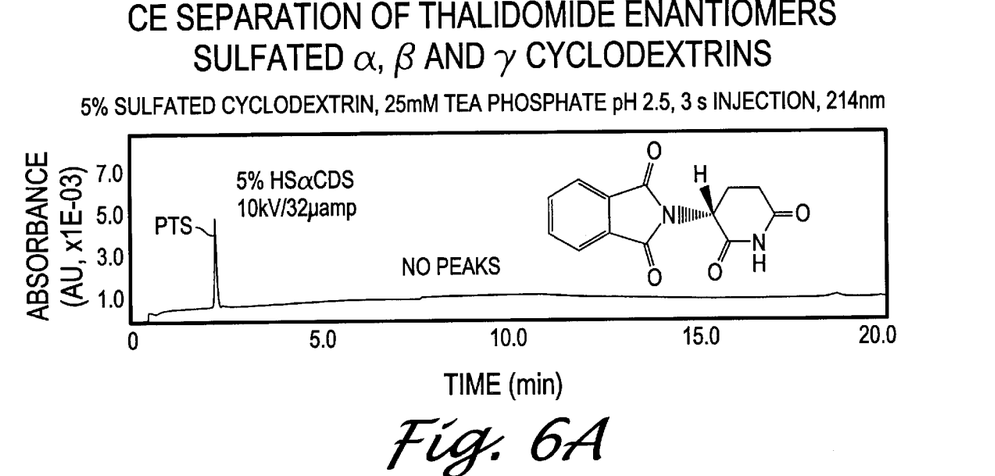
Figure 6B:
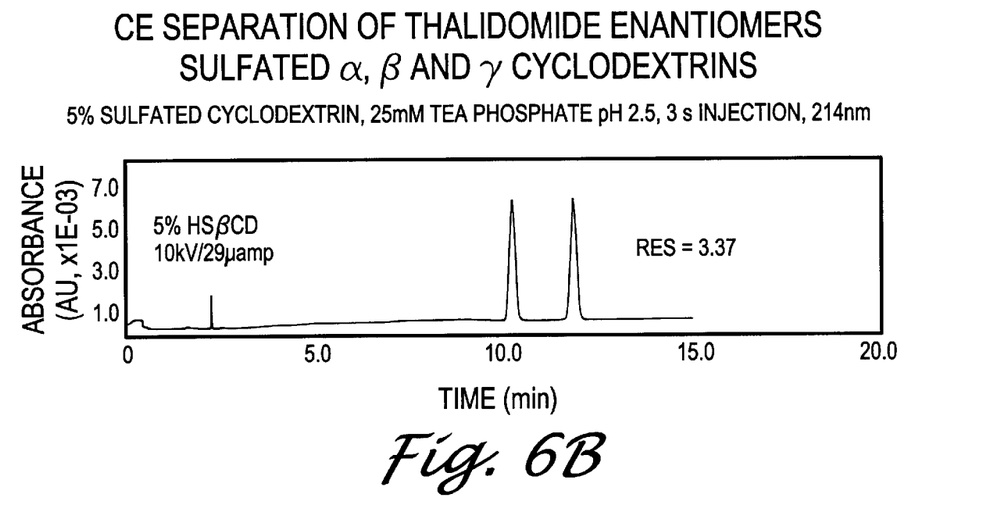
Figure 6C:
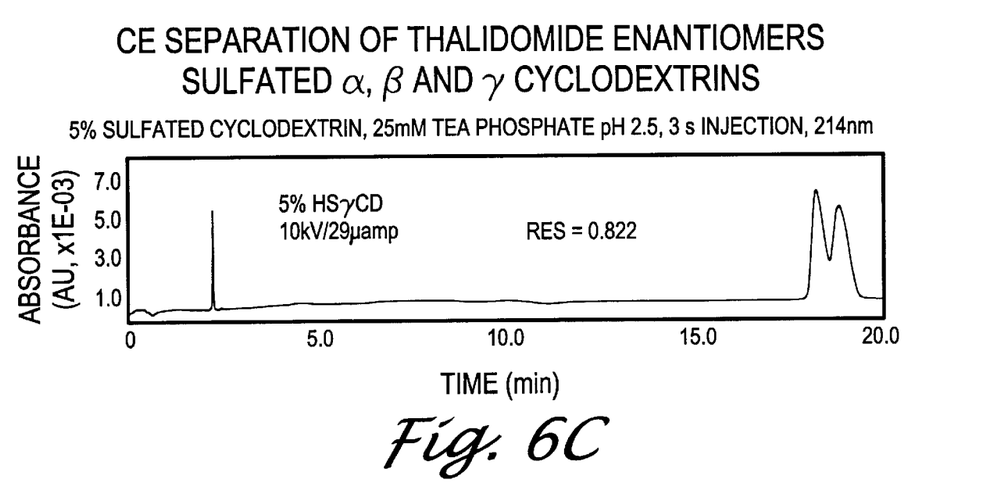

This example shows that the range of chiral compounds that can be separated is extended by including highly sulfated α- and γ-cyclodextrins (HSαCD and HSγCD, respectively) in the CE-based chiral separations. The results in Table 4 show that the separations produced by the three different HSCDs complement each other to cover a wide variety of neutral and basic drugs. The HSγCD was found to be particularly effective in separating enantiomers of pharmacologically important phenethylamines. Examples of the chiral CE analysis of amphetamine and thalidomide are presented in FIGS. 5 and 6, respectively. Optimal resolution for amphetamine (R=21.68) was obtained using HSγCD, whereas HSβCD gave the best separation of thalidomide (R=3.37).

TABLE 4

Resolution of Racemic Compounds with Sulfated α-, β-, and γ-Cyclodextrins (5% in TEA phosphate pH 3.0)

| Neutrals | HSαCD | HSβCD | HSγCD |
|---|---|---|---|
| Thalidomide | No peaks | 3.37 | 0.82 |
| Chlorthalidone | 5.36 | 1.79 | 0.00 |
| Mephenesin | No peaks | No peaks | 1.19 |
| 5-(4-Methylphenyl)-5-phenyhydantoin | No peaks | 1.64 | 1.14 |
| α-Methyl-α-phenylsuccinimide | No peaks | 2.80 | 0.00 |
| Amines | | | |
| Amphetamine | 2.87 | 2.83 | 21.68 |
| Methamphetamine | 1.49 | 2.16 | 11.58 |
| 3,4-Methylenedioxyamphetamine | 0.00 | 1.06 | 7.42 |
| 3,4-Methylenedioxymethamphetamine | 0.77 | 0.82 | 5.39 |
| Ephedrine | 4.47 | 2.59 | 6.80 |
| Arterenol | No peaks | 0.00 | 1.69 |
| Metaproterenol | 0.34 | 1.00 | 3.70 |
| Terbutaline | 0.00 | 1.53 | 3.12 |
| Fluoxetine | 6.00 | 1.22 | 8.44 |
| Atropine | 0.00 | 3.33 | 0.39 |
| Miconazole | 0.73 | 2.18 | 0.00 |
| Propranolol | 3.08 | 0.00 | 0.00 |
| Ketamine | 1.35 | 0.53 | 0.71 |
| Verapamil | 4.13 | 1.46 | 1.67 |
| Zwitterions | | | |
| Dopa | No peaks | 11.75 | 8.38 |
| Carbidopa | No peaks | 10.35 | No peaks |

Although the present invention has been described in considerable detail with reference to certain preferred versions thereof, other versions are posssible. For example, the cyclodextrins could be modified with other negatively charged constituents, such as phosphate, or a positively charged constituent, like a quaternary amine. Moreover, CE separations may be conducted using different buffers or pH conditions to improve the resolution of the charged CD complexes. Therefore, the spirit and scope of the appended claims should not be limited to the description of the preferred versions contained herein.

We claim:
1. A charged cyclodextrin, selected from the group consisting of:
   an alpha cyclodextrin,
   a beta cyclodextrin having at least about 12 modified hydroxyl groups, and
   a gamma cyclodextrin,
   wherein said cyclodextrin comprises a charged substituent at the 6-position of each glucose unit of the cyclodextrin, at least one modification of a secondary hydroxyl at the 2-position, and an unmodified secondary hydroxyl at the 3-position.
2. A charged cyclodextrin having the following formula:

selected from the group consisting of:
   a) a cyclodextrin in which n is 6 or 8, at least about one $R^1$ group is a modified hydroxyl, and less than about n $R^1$ groups are hydroxyl; and
   b) a cyclodextrin in which n is 7, at least about 5 $R^1$ groups are modified hydroxyls, and less than about 3 $R^1$ groups are hydroxyl;
   wherein the modified hydroxyl comprises a sulfate, carboxylate, phosphate, or quaternary amine substituent.
3. A charged cyclodextrin according to claim 1 or 2 wherein the modified hydroxyl groups are sulfated.
4. A highly sulfated alpha cyclodextrin, said alpha cyclodextrin possessing at least about 7 sulfate substituents, and an unmodified secondary hydroxyl in the 3-position, wherein at least one substituent is at the 6-position of each glucose unit of the cyclodextrin.
5. A highly sulfated beta cyclodextrin, said beta cyclodextrin possessing at least about 12 sulfate substituents, and an unmodified secondary hydroxyl in the 3-position, wherein at least one substituent is at the 6-position of each glucose unit of the cyclodextrin.
6. A highly sulfated gamma cyclodextrin, said gamma cyclodextrin possessing at least about 9 sulfate substituents, and an unmodified secondary hydroxyl in the 3-position, wherein at least one substituent is at the 6-position of each glucose unit of the cyclodextrin.
7. A composition comprising a sample, a charged cyclodextrin according to claim 1, and an electrophoresis buffer, wherein the sample is a small chiral molecule.
8. A composition according to claim 7, wherein sample comprises a neutral compound or an amine.
9. A composition according to claim 7, wherein the concentration of the sample is from about 0.1 to 10 mM.
10. A composition according to claim 7 wherein the cyclodextrin is present in molar excess relative to the sample.

11. A composition according to claim 7, wherein the sample comprises a drug or pharmaceutical compound.

12. A composition according to claim 7 further comprising an internal standard.

13. A composition according to claim 8, wherein the internal standard is 1,3,6,8-pyrenetetrasulfonic acid or its salt.

14. A kit for separating chiral compounds comprising at least two highly sulfated cyclodextrins selected from the group consisting of:
   a) an alpha cyclodextrin possessing at least about 7 sulfate substituents;
   b) a beta cyclodextrin possessing at least about 12 sulfate substituents;
   c) a gamma cyclodextrin possessing at least about 9 sulfate substituents,
   wherein said cyclodextrin comprises a charged substituent at the 6-position of each glucose unit of the cyclodextrin, at least one modification of a secondary hydroxyl at the 2-position, and an unmodified secondary hydroxyl at the 3-position.

15. A kit according to claim 14, further comprising at least one electrophoresis buffer.

16. A kit according to claim 14, further comprising an internal standard.

17. A kit according to claim 14, further comprising at least one capillary.

18. A kit according to claim 15 further comprising at least one pH adjusting agent.

19. A composition comprising:
   a charged cyclodextrin, selected from the group consisting of:
      an alpha cyclodextrin,
      a beta cyclodextrin having at least about 12 modified hydroxyl groups, and
      a gamma cyclodextrin,
   wherein said cyclodextrin comprises a charged substituent at the 6-position of each glucose unit of the cyclodextrin, at least one modification of a secondary hydroxyl at the 2-position, and an uinodified secondary hydroxyl at the 3-position; and
   an internal standard.

20. The composition according to claim 19, wherein the internal standard is 1,3,6,8-pyrenetetrasulfonic acid or its salt.

21. A composition comprising a charged cyclodextrin of claim 1 and an electrophoresis buffer.

22. A composition of claim 21, wherein the electrophoresis buffer is acidic.

23. A composition according to claim 21, wherein the concentration of the cyclodextrin is between about 1% and 20%.

24. A composition according to claim 22, wherein the pH range of the acidic buffer is between about 1 to about 5.

25. A composition. according to claim 21, wherein the electrophoresis buffer comprises an electrolyte selected from the group consisting of phosphates, acetates, and citrates.

* * * * *